Figure 1:
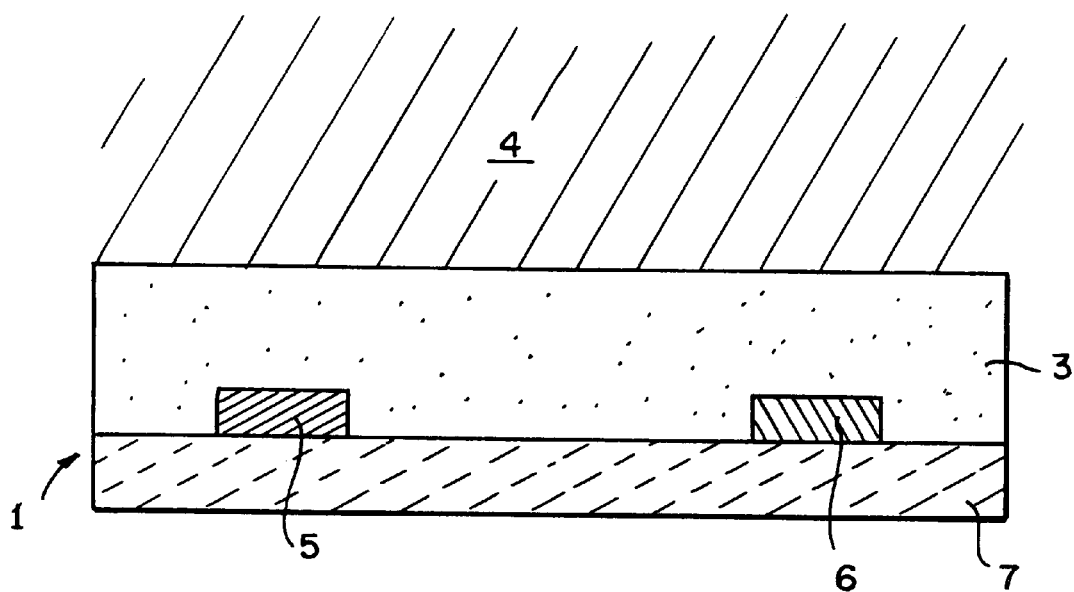

United States Patent

Choulga et al.

[11] Patent Number: 6,004,442
[45] Date of Patent: Dec. 21, 1999

[54] ANALYTE-SELECTIVE SENSOR

[75] Inventors: Alexandre Choulga; Benedikt Ahlers; Karl Cammann, all of Munster, Germany

[73] Assignee: Institut Fur Chemo- Und Biosensorik Munster E.V., Munster, Germany

[21] Appl. No.: 08/817,522

[22] PCT Filed: Oct. 17, 1995

[86] PCT No.: PCT/DE95/01458

§ 371 Date: Nov. 4, 1997

§ 102(e) Date: Nov. 4, 1997

[87] PCT Pub. No.: WO96/12176

PCT Pub. Date: Apr. 25, 1996

[30] Foreign Application Priority Data

Oct. 18, 1994 [DE] Germany ............................ 44 37 274

[51] Int. Cl.[6] ..................................................... G01N 27/12
[52] U.S. Cl. ........................................... 204/416; 204/415
[58] Field of Search ...................................... 204/415, 416

[56] References Cited

U.S. PATENT DOCUMENTS

| 4,214,968 | 7/1980 | Battaglia et al. . |
| 4,334,880 | 6/1982 | Malmros . |
| 4,798,664 | 1/1989 | Yamaguchi et al. ................. 204/418 |
| 5,032,363 | 7/1991 | Simon et al. ..................... 422/82.03 |
| 5,200,051 | 4/1993 | Cozette et al. ..................... 204/403 |
| 5,337,018 | 8/1994 | Yamagishi . |

FOREIGN PATENT DOCUMENTS

| 0 096 095 | 6/1982 | European Pat. Off. . |
| 677295 | 4/1991 | Switzerland . |
| 2 137 361 | 10/1984 | United Kingdom . |
| 2139761 | 11/1984 | United Kingdom . |
| 2 204 408 | 11/1988 | United Kingdom . |
| 2 208 006 | 2/1989 | United Kingdom . |
| WO 93/06237 | 4/1993 | WIPO . |

Primary Examiner—Terrence R. Till
Assistant Examiner—Jennifer McNeil
Attorney, Agent, or Firm—Barnes & Thornburg

[57] ABSTRACT

The invention concerns an analyte selective sensor for the qualitative and/or quantitative determination of ions or substances contained in solution. The proposed sensor (1) comprises at least one analyte-specific layer (3) deposited on an inert carrier (7) and in contact with the solution; this analyte-specific layer consists of a liquid, solid or semi-solid material and is in contact with at least two electrodes (5, 6). The layer (3) selectively removes the analyte from the solution so that its own electrical characteristics, such as resistance, conductivity, admittance or impedance, change as the analyte is taken up.

51 Claims, 10 Drawing Sheets

ANALYTE-SELECTIVE SENSOR

CROSS-REFERENCE TO RELATED APPLICATIONS

This application is a U.S. national phase counterpart of international application Ser. No. PCT/DE95/01458 filed Oct. 17, 1995, which claims priorrity to German Application Ser. No. P 44 37 274.4 filed Oct. 18, 1994.

The invention relates to an analyte-selective sensor comprising an analyte-specific layer, which is so modified that ions or neutral species contained in solutions can come into contact with the layer, so that then an alteration in the electrical properties occurs.

In order to detect ions in solutions the potentiometric ion-selective electrode is widely used (Camann, K. Die Arbeit mit Ionenselektiven Elektroden, [Working with Ion-selective Electrodes], 2nd ed., Springer Verlag: Berlin, Heidelberg, N.Y., 1977)). Ion-selective electrodes are electrochemical sensors by means of which the concentration (more precisely the activity) of specific ions can be detected by means of a potential difference. The ion-selective potential difference occurs at the phase boundary between electrode material/electrolyte and, according to the Nernst equation, depends on the activity of a specific ion in the solution.

The necessity for a reference electrode is the decisive disadvantage in the use of potentiometric measurements for detecting ion activities in solution. Other than for resistance and capacity, the absolute values of the electrical potential have no physical meaning, as the potential can only be defined with respect to a reference value. In electrochemistry such a reference value is usually provided by the potential of the reference electrode.

The other basic restriction in potentiometric analysis methods relates to the composition of the ion-selective membrane. The requirements of the nature of the specific bond and/or of the complexing points within the membrane are to be set in such a way that the potential difference is selectively built up at the boundary surface membrane/solution in dependency on the presence of a specific species in the solution. For example, this bond should not be too strong, so that a sufficiently rapid exchange of the detected species between the membrane phase and the solution is possible.

Next to the potentiometric methods, the most frequently used electrochemical analytical methods are those which measure the current flow by means of an appropriately prepared or modified conductive or semiconductive collector electrode. The potential of this electrode is fixed by that of the reference electrode. The current flow measured results from the electrochemical redox reaction which takes place at the boundary surface between collector electrode/solution. In addition to this necessary reference electrode, the use of these measurement methods is also restricted by the fact that the species measured at the working potential applied to the collector electrode must be electroactive, and thus only a restricted number of analytes can be measured. Moreover this potential must be different from that of the interfering species. The latter frequently represents a problem, as many chemical or large groups of chemical compounds have very similar redox properties. On the other hand, the electrical potentials necessary for many compounds lie outwith the practicably usable range.

Among the non-electrochemical methods most used for specific recognition of charged and neutral species are the various types of liquid chromatography. In this case the sample to be analysed is brought into contact with a so-called stationary phase, e.g. a polymer layer, which specifically bonds or retains the detected species. The strength of this bond determines the retention time of the analyte within the chromatographic column. When tailor-made stationary phases are used, a large number of species can be identified. However, this type of analytical measuring arrangement is extremely complex and expensive.

The other important class of analytical methods for detecting charged and uncharged species in gaseous or liquid medium uses measurement of the resistance or capacitance. Alterations in the conductivity or of the dielectric properties of a layer of a sensitive material are indicated in dependency on the interactions with the detected species. Thus resistance and capacitative sensors are widely used in the field of detection of gases.

Contrary to this, the use of such sensors in chemical analyses in liquids is only occasionally encountered. Measurements of the total conductivity of electrolyte solutions are only of limited analytical importance, because they generally lack specificity. Such a method is described by R. S. Sethi et al. in GB 22 04 408 A. In this document a conductometric enzyme biosensor is proposed which has interdigital finger-like electrodes (IDE), which are covered by a membrane of immobilised urease. In the presence of urea in the test solution, the use of densely-arranged electrodes permits measurement of the conductivity of the solution with which the enzyme layer is saturated, insofar as the conductivity changes specifically to the hydrolysis of the urea which is catalysed by the urease. Among the weaknesses of such biosensors are the drastic reduction sensitivity of the bicsensor with increasing buffer capacity and/or ion strength (conductivity) of the solution.

The document WO 93/06 237 describes the use of IDEs for measuring the alteration in conductivity of a layer of electroactively conductive polymer (polyaniline, polypyrrol). These alterations result from the interaction of the functional redox groups of the polymer with the species of interest in the solution, or with species which result from an enzyme reaction in the layer of the immobilised enzyme which is applied from above on to the layer of the said polymer.

L. S. Raymond et al. describe, in GB 21 37 361, an arrangement for capacitive detection which contains the following components:

(I) a condenser consisting of two IDE's;

(II) a first layer of electrically insulating material, which covers the electrically conductive electrode and shields it from the solution to be analysed;

(III) a second layer of a material which covers the first layer, the second layer being permeable to a specific non-aqueous substance in a solution, which causes, by its entry into the electrical field between the IDEs, an alteration in the capacitance of the condenser.

The second layer contains for example the substance valinomycin, which is permeable to potassium ions. The interdigital electrodes measure the alteration in capacitance as a consequence of the specific absorption of ions into the valinomycin layer.

The document GB 21 37 361 however provides no description of the composition of the membrane, i.e. there are no details on the conditions which are necessary in order to ensure the required permeability of this sensitive second layer with respect to the species of interest. On the other hand, such conditions to a large extent restrict the number of detectable species. The necessity for shielding the conductive electrodes by an insulating layer renders difficult the manufacture of the transducer due to the high quality requirements of such a layer, and at the same time impairs the sensor sensitivity. A further problem is an unavoidable abrupt alteration in the dielectricity constants of the measuring layer in dependency on the composition of the solution to be analysed.

Proceeding from this point it is the object of the present invention to propose a novel sensor concept and corresponding sensors which permit ions or neutral species contained in solution to be detected quantitatively and/or qualitatively via an absolute measurement, so that reference electrodes can be omitted.

This purpose is achieved by the characterising features of claim 1. The sub-claims indicate advantageous further developments.

Thus it is proposed according to the invention to use a sensor which has, on a carrier, an analyte-specific layer of a liquid, solid or semi-solid material which is so formed that, upon contact with the ions or materials contained in the solution, it changes its bulk electric properties such as resistance, conductivity, admittance or impedance.

Thus, for measurement of the electrical properties of the analyte-specific layer, it is provided that preferably at least two electrodes are used, which are in contact with the analyte-specific layer. For this purpose the analyte-specific-laver is formed directly on the conductor surface. Standard two- or four-electrode arrangements can be used for this type of measurement.

The conductive materials used to produce the solid or semi-solid or porous measuring electrodes can be materials which, due to the mobility of electrodes or of defect points, have properties of an electrical conductor, of a semi-conductor or of a defect point conductor. Examples of this are:

noble metals (Ag, Au, Pt, Pd, . . . );
other sufficiently chemically stable metals (Ni, Ta, Ti, Cr, Cu, V, Al, . . . );
conductive pastes and epoxy resins containing particles of metal or graphite;
materials on a carbon basis (carbon fibres, glass carbon, graphite);
highly-doped silicon (poly-Si);
conductive polymers (polypyrrol, polyaniline, polyacetylene);
Assembled conductive polymers which contain particles of metal or graphite.

The conductors can be free-standing, for example in the form of rods, wires or meshes or can be embedded in plastic or other insulating carriers which leave free only the membrane contact surface. The exposed portion can for example be present in the form of discs or strips.

As an alternative, the conductors can also be formed on an insulating carrier in the form of thick or thin layers, produced with the aid of screen printing, by chemical or electrochemical polymerisation or separation (the latter in the case of metals), by vacuum evaporation, sputtering or other techniques of thick and thin layer technology. The conductors applied to an insulating carrier can for example be present in the form of strips, circles, discs or interdigital electrodes (IDE). The conductors can be located on the same or on the opposite sides of the carrier, in a plane or separated vertically from one another.

The surface of the measuring electrode need not necessarily be smooth or polished. It may be deliberately made rough, in order to produce a better contact with the layer and to reduce the boundary surface resistance. A possible solution is the use of platinised platinum electrodes or of chloridised silver electrodes.

In the case where increased electrochemical boundary resistances occur between the conductors and the layer, a further preferred embodiment proposes an additional layer between the conductors and the analyte-selective layer, which has substances forming redox pairs in order to suppress the boundary surface resistance. Such substances forming redox pairs suppressing the boundary surface resistance are already described in CH 677 295. Reference is therefore expressly made to the disclosed content. The layer thickness of this layer in this case lies in the range of 0.1 $\mu$m to 100 $\mu$m.

As no electron transfer is necessary between the electrodes and the analyte-specific layer during AC measurements, a direct contact as described above is not necessary between the surface of the conductor and the layer. Thus it is possible to carry out such measurements with electrodes which are separated by an air gap or an insulating layer from the analyte-selective layer, with the so-called phenomenon of capacitive coupling. It is likewise possible to use inductive coupling for contactless measurements of the electrical properties of layers. In this case the layer is placed in a coil through which a current then flows. Turbulent currents are built up in the layer and cause a power loss in dependency on the layer conductivity. A further possibility resides in the use of two coils, which are connected in the sample by a circuit current.

The factor essential to the invention in the analyte-selective sensors here proposed is the analyte-specific layer. This layer is so modified that it changes its electrical properties in the presence of ions or materials contained in solutions. The alteration in the electrical properties of the analyte-specific layer are in this case to be ascribed to the distribution of the ion or material to be detected between the solution and the layer. In this way the electrical properties, such as resistance, conductivity, admittance or impedance, now change.

In this way the analyte-selective sensors according to the invention reveal the following decisive advantages in comparison to prior art:

1. In the sensors according to the invention, no reference electrode is required, as the measurements of such electrical properties as conductivity or admittance, contrary for example to potential measurements in potentiometry, are absolute measurements.

2. The sensors can be constructed as highly-integrated solid body complete systems, which simplifies their manufacture, miniaturisation and utilisation.

3. The sensor design is compatible with microelectronics, particularly with IC technology, and thus permits the production of such sensors in large numbers at low cost, including disposable sensors.

Possible sensor arrays can be easily integrated on a substrate together with electronic signal processing systems.

4. The method of operation of the sensors leads to an extension of the detection range of the species to be detected in comparison to traditional electrochemical detection techniques, and to an enlarged selection of materials which can be used as selectively bonding components in the sensors. These sensors, in contrast to potentiometric sensors, permit the detection of analyte concentrations in solutions with a very high ion strength. As long as the measurements of the layer properties such as resistance or conductivity are absolute measurements, no restrictions in practice occur upon the appearance of irreversible extractions.

The sensors described in the present invention can then be used as dosimeters. An example of this is the detection of traces of toxic components, e.g. of heavy metal ions.

5. Measurement of the solution composition in closed vessels, e.g. in melt-sealed glass bulbs, is possible with the sensors. A condition is that the sensitive membrane is located within the vessel, e.g. on the inner surface of the walls, and that the alterations in the electrical properties of the membrane are measured from outside the vessel, using contactless measuring techniques.

According to the invention, the layer consists of a liquid, semi-solid or solid component (material), so that the layer, due to its bulk properties or to the presence of analyte-specific coupling elements, is capable of extracting the analytes from a solution. The analyte-specific layer preferably consists of a polymer which has or contains ion-selective or molecule-selective coupling members, so that the analyte is selectively extracted out of the solution into this polymer membrane layer. The term coupling members according to the present invention is understood to cover, among other things, functional groups, ion exchangers, complexing groups or chelate groups, cage compounds (e.g. cyclophanes, crown ethers, antibiotics, cyclodextrines), antigens or antibodies, natural or synthetic polypeptides, lectins, specifically bonding proteins, receptor proteins, lipids and tensides. The term coupling members thus includes all these compounds or residues which are capable of bonding the ions or neutral particles contained in the analyte. The layer can be a polymer which itself has these coupling members, i.e. the polymer itself has corresponding residues or functional groups, or these coupling components are added to the polymer. A selective alteration in the ionic conductivity is then connected by the selective extraction. In this case it is not decisive whether a reversible or irreversible analyte extraction or bond takes place in the analyte-specific layer, as the measurements of the layer properties, such as resistance or conductivity, are absolute measurements. In the case of irreversible analyte extractions or bonds, the sensor according to the invention can be used as a dosimeter, i.e. the alteration in the electrical properties of the layer is to be understood as an imperical parameter (dose) of the analyte traces in a medium, to which the sensor is exposed over a long period of time.

According to the invention it is proposed that the analyte-specific layer be applied on to a carrier, e.g. on to gass, metal, ceramics, sapphire, plastic or polymer in the form of films. The techniques of application of the polymer membrane layer are known per se from prior art. The following should be named as appropriate separation methods:

Separation from the solution, dripping, dip-coating, spraying, chemical, photochemical or electrochemical polymerisation, spin-coating or photolithography.

In this case it can be advantageous to use, for liquids which form the analyte-specific layer, a porous matrix/carrier (e.g. filter papers, textiles, microporous glass) for stabilisation purposes.

According to the invention it is possible for a liquid to function as an analyte-specific layer. Specificity during extraction of the target analyte can be controlled by specific bulk properties of the liquid, such for example as liphophily. In this case this liquid can be an organic solvent which is not, or is only restrictecly soluble in water, so that target analytes are extracted from aqueous media into this liquid, which forms the analyte-specific layer. The following liquids are named as examples:

non-polar solvents such as tetrachloromethane, chloroform, hexane, toluol, and most of the aromatic and saturated aliphatic hydrocarbons.

According to the invention it is possible to control the specificity during extraction of the target analyte by specific bulk properties of the analyte-specific polymer membrane layer, such as polarity. In this way lipophilic components can be extracted from an aqueous phase into a membrane phase, which likewise comprises lipophilic components.

The polymer is an aliphatic main chain with non-polar or low-polar substituents. In this case polymerisates should be named, which form the polymer layer on the transducer. Those homopolymerisates or copolymerisates are preferred which originate from the monomer units of alkenes, and if necessary carry non-polar or low-polar substituents:

The following are named as examples for $R_1$ substituents: $R_1=$ —H, —F, —Cl, —BR, —NO$_2$, —COR, —COOR (bound to the polymer main chain via the oxygen atom or carbon atom), carboxylic acid nitryl groups, carboxylic acid amide groups, aliphatic/aromatic ether groupings, aromatic/heteroaromatic residues. The polymer material can be of a low-molecular up to extremely high-molecular composition, but is however preferably high-molecular.

Among the known homopolymerisates or copolymerisates on the basis of monomer units which originate from an alkene, those ones are specially preferred which are a vinylhalogenide homopolymerisate, a vinylhalogenide copolymerisate, a vinylidenehalogenide homopolymerisate or a vinylidenehalogenide copolymerisate. In these homo- or copolymerisates the halogen atom is preferably a chlorine atom.

The following polymer materials (corresponding homo/copolymerisates) are considered as polymers for the solid or semi-solid membrane:

polyesters polyamides polyurethanes silicon containing polymer material, preferably a silicon resin or silicon rubber;

cellulcse derivates such as cellulose ether or cellulose ester.

Solid or semi-solid layers produced from such polymers can also if necessary contain organic, lipophilic, water-insoluble liquids, preferably ethers and esters of aliphatic alcohols.

Alternatively to this, detection of polar additives in an organic medium, e.g. of oils, is possible by extraction into ionically-conductive solid or semi-solid polymer films, which are not miscible with the measuring solution.

In this case the polymer of the layer should be a polymer or copolymer with intensely hydrophilic side groups, or have only small proportions of low-polar or hydrophobic groups. Solid or semi-solid layers produced from these polymers can likewise contain an aqueous electrolyte solution.

Such a film can for example be a solid polyethylene oxide film, which contains alkali salts as ionic additives (supporting electrolytes), preferably lithium salts with the anions CF$_3$CO$_2$—, CF$_3$SO$_2$—, C$_6$F$_{13}$SO$_3$—, HgI$_3$—, AsF$_6$. The other appropriate polymers which possess a high degree of chain mobility, are for example polyphosphazene (1) and polysiloxane (2) with the side groups R which have cation-complexing and ion-pair-separating properties, such for example as is the case with oligoalkyl ethers. The polymers mentioned can be described by the following general formulae:

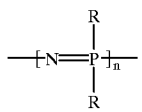  (1)

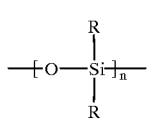  (2)

Polymers are preferred with R=OCH$_2$CH$_2$OCH$_2$CH$_2$OCH$_2$.

A layer can be produced on the other side also in such a way that the specific extraction of the analyte into the membrane phase is determined by the affinity of the analyte molecule to morphologically (structurally) fixed bond points within the layer. This may be achieved for example in that the layer is produced in the presence of free analyte molecules, e.g. by chemical, photochemical or electrochemical polymerisation. There is obtained a non-covalent accumulation of the analyte on monomeric units, i.e. via ionic, hydrogen bridge, hydrophobic or charge transfer interactions, opposed to the respective sides of the analyte molecule. The analyte is later removed by washing or hydrolysis, leaving behind its "prints" produced on a molecular scale during layer formation.

These "prints" now function as bond points with an increased affinity to the analyte. The affinity is dependent on the distribution of the charge or other functional groups in the analyte molecule and on its shape and size. The affinity of such layers to specific species can among other things be controlled via the conditions of layer formation or via the ratio of the layer components. The degree of occupation of the "print" bonding points by analyte molecules can for example influence the ionic conductivity of the layer, and these alterations can be measured using the means forming part of the invention.

The layers based on the affinity principle can be prepared in such a way that in addition they are capable of bonding specifically charged or neutral species, or of differentiating between optical isomers.

Such membranes can consist for example of electrochemically produced polymer films. For films made of polypyrrol and polyaniline it is known for example from prior art that the selectivity sequence of the anion exchange is determined by the counter-ion taken up during synthesis from the aqueous or organic solution.

The base components which may be manufactured by electropolymerisation are as follows:

heteroaromatic/aromatic compounds, e.g. thiophenes, pyrrols, phenols, anilines, napthalenes, anthracenes, carbazoles.

The counter-ions used during electropolymerisation can for example be inorganic or organic ions, polyions, biomolecules and their fragments. The hydrophobicity of such a material can be controlled either by the use of monomer units modified with hydrophobic groups or by the absorption of hydrophobic counter-ions. The molecular recognition properties can be optimised by the addition of functional groups to the basic monomers, by alteration of the proportion of the monomer units in copolymers, or by alteration of the degree of cross-linking. In order to prevent interferences in the measuring process which are ascribed to alterations in the internal electronic conductivity of the polymers, the polymers can be electrochemically hyperoxidised, so that an electronically non-conductive but tonically conductive material is generated. Such a treatment at the same time prevents an excess of anionic species in the polymer film. Alternatively, the molecular selectivity of the film may also be co-ordinated by control via the redox condition, i.e. with application of a direct-current potential.

It is proposed for the embodiments described above that the analyte-specific layer consists of a polymer which has ion-selective or molecule-selective coupling points, so that the analyte can be selectively extracted from the solution into the layer. It is proposed for this embodiment that the polymer layer is an ion conductor.

According to the invention these polymers can be complex-forming polymers, which can form polymeric chelate formers, i.e. products which can form chelates. They contain corresponding chelatising functional groups in a covalent bond to polymers, which can be non-cross-linked or cross-linked. Complex formation of these groups with metal ions can be effected both intra-molecularly and intermolecularly.complexing groups (ligands) of conventional complexing-forming polymers are residues of iminodiacetic acid, hydroquinoline, thiourea, guanidine, dithiocarbamate, hydroxamic acid, amidoxim, amino, phposphoric acid (cycl.) polyamino, mercapto, 1,3-dicarbonyl, and crown ether with in part very specific activities with respect to ions of various metals.

Base polymers of the complex-forming polymers are, in addition to polystyrolene, polyacrylates, polyacrylnitriles, polyvinylalcohols, polethylenimines. Production of the complex-forming polymers is preferably effected in polymer-analogous reactions on cross-linked polyvinyl compounds.

By means of polymer-analogous reactions, complex-forming polymers can be obtained both from natural polymers such as cellulose, starch, lignin or chitin, and also from modified natural polymers, e.g. humic acids. Likewise, the compounds may be bonded covalently to the polymer, such as cage compounds, (e.g. cyclophanes, crown ethers, antibiotics, cyclodextrines), antigens or antibodies, natural or synthetic polypeptides, lectins, specifically bonding proteins, lipids and tensides. Examples of such polymers are: polysaccharides with active ligands, polycrown ether; polycrown vinyls; polyether copolymers with active ligands; polysaccharides, polysilocanes and polyacrylates with chiral selectors.

Tensides, colloidal gold, graphite, glass or inorganic microoarticles or pearls can be included in the polymer films and serve as molecular carriers.

The selective bonding of neutral or charged species, e.g. alkali metal ions, $Mg^{2+}$, $Ca^{2+}$ or transitional metal ions, to specific functional groups in the polymer layer can cause alteration in the morphology and the pore size, i.e.

(a) increase/decrease in the cross-linking of the matrix polymer or (b) conformative, molecular alteration of the components of the membrane layer.

Alterations in the morphology can lead to alteration in the electrical properties of the membrane layer, e.g. of the ionic conductivity. This is the case with some gels, proteins, particularly receptor proteins, lipids and tensides, which contain functional groups which are capable of bonding anions or cations, or which are sensitive to lipophilic components in the sample.

Likewise, polymer films can be used which contain ligands covalently bound to the polymer basic structure, which are capable of completing ions. These films can be cross-linked, e.g. by transitional metal ions, if these ions form complexes or chelates with the liaands contained in the polymer at various points of the polymer chain.

Cation receptor polymer layers, e.g. multi-phase polymer layers, which are sensitive to $Ca^{2+}$, can contain poly-L-glutamic acid chains in a block copolymer.

Among the molecules which are capable of undertaking conformative alterations induced by anion or cation bonding there should be named polyions such as proteins and synthetic or natural polypeptides. In particular the two classes of polyanionic macromolecules, proteoglycanes and acidic glycoproteins show the characteristics named above, for example for sodium and calcium. These macromolecules represent polyanions and in accordance with their carboxylised, silaic or sulphate groups.

When the polymer films described above contain dispersed conductive particles, contraction of the film causes an increase in the film conductivity in accordance with the increased contact between the particles. The conductive particles preferably have a size of less than 10 μm, at best smaller than 1 μm and for example consist of a semiconductor, metal or graphite.

The analyte-specific layer can have an ordered structure (i.e. the components of the medium form a liquid crystal phase), a partly ordered structure (e.g. in the multi-double structures of films which are formed from polyionic complexes), or an amorphous structure. During extraction of the analyte into the membrane phase an effect on the conditioning of the membrane phase is possible, e.g. a disorganisation, so that its bulk electric properties are influenced.

The abovementioned multi-double structures can for example be formed from polyionic complexes between quaternary ammonium ions including tensides and lipids, and from polyions, such for example as polystyrol sulphonate and polyvinyl sulphonate. The components of such a film are for example dioctadegyl dimethyl-ammoniumbromide ($2C_{18}N^+2CBr$) and sodiumpoly styrol sulphonate ($PSS-Na^+$).

Ion exchangers and ionic polymers can likewise be used as a sensitive layer material in the sense of the present invention, insofar as the ion exchange has as a result an alteration in the electrical properties of the layer for the detected ion.

In this invention the definition of an ion exchanger used is that according to "RÖMPP CHEMIE LEXIKON, Georg Thieme Verlag Stuttgart, 9th ed., vol. 3 pages 2026–2028".

The characterising feature of an ion exchanger and ionic polymer is the presence of a large quantity of hydrophilic groups which are bonded to the polymer. These groups can, in cation exchanger resins, for example be $—SO_3H$ and $—COOH$, and in ion exchange resins, for example quaternary ammonium groups. Such polymers, e.g. persulphone polymers such as Nafion or Eastman Kodak AQ-polymers, can also contain substantial hydrophobic areas. In this way films with a heterogeneous structure are formed, with separate hydrophilic and hydrophobic regions. Characteristic of these materials is the fact that they themselves internally dilute by the inclusion of water and prevent a local ionisation, with the result of a conductivity close to that of aqueous electrolytes.

According to the present invention, the term "ionic polymers" relates to polymers which have basic or acidic functional groups bonded to or in the basic structure of the polymer.

The definition used is that according to "RÖMPP CHEMIE LEXIKON, Georg Thieme Verlag Stuttgart, 9th ed., vol. 3 page 2038". Among others, salts of carboxy, sulphpnic acid, phosphonic acid, ammonium or phosphonium groups can function as ionic groups of the ionic polymers.

According to the invention the ionomers forming the sensitive layer can in particular belong to the following groups:

copolymers of ethylene, acrylic or metacrylic acid;
carboxyelastomers;
terpolymers;
terpolymer ethylene-propylene-diene sulphonate;
substituted polyvinyls such as polyacrylates, particularly polyacetates or butyrals or polyvinylimidazoles;
perfluoropolymers, particularly perfluorosulphonates,
polyampholytes A further preferred embodiment now proposes that the analyte-specific layer, in addition to the polymer materials and/or liquids described above, also contains ion-selective or molecule-selective coupling members. Accordingly the analyte-specific polymer layer can on the one hand consist of a polymer which has itself corresponding coupling members, in order to enable a selective extraction of the analyte, on the other hand however it is also possible for the layer, as described above, to contain a polymer material and/or liquid, and in addition for ion-selective or molecule-selective coupling members to be added. Such coupling members are preferably complex formers for cations/anions/neutral particles. Such complex formers then enable complexing and a transfer mobility of ions or neutral molecules in the lipophilic, sensitive layer.

This complex former should have lipophilic properties and form charged or uncharged complexes with cations/anions/neutral particles. Furthermore, anion/cation exchangers likewise represent components in the layer which cause mobility of ions within the layer. Both the complex formers or cations/anions/neutral particles and also anion/cation exchangers with their lipophilic properties can be present together in the layer.

Many examples are described in the literature for the abovenamed ion-selective or molecule-selective components with lipophilic properties, e.g. those used in ion-selective membranes or ion-selective electrodes, extraction or meshing processes.

The following are named here as examples of ion-selective components:

cation exchangers: dialkyl phosphates, tetraarylborates and their salts, e.g. tetraphenylborate and its silver and alkali salts, such as sodium tetraphenylborate. The phenyl cores of the tetraphenylborates can be unsubstituted or substituted, preferably monochloro-substituted in the para position.

anion exchangers; trialkyl methyl ammonium salts, cationic metal complexes.

complex formers for cations, cyclic, e.g. macrocycles such as crown ether (alkali selectivity), natural antibiotics, valinomycin—potassim selectivity, nonactin—ammonium selectivity) non-cyclic, e.g. dicarboxylic acid amides, (high selectivity for alkali/hardness ions), tridodecylamin ($H^+$—sensitivity.

complex formers for anions: e.g. guanidinium compounds, complexing of oxo-anions such as phosphate or nitrate.

complex formers for neutral particles: e.g. derivates of boric acid such as boron acid (complex formation with glucose) calixarene (complexing of organic compounds such as tetrachlorethene).

A further preferred embodiment then proposes that plasticiser be added to the solid or semi-solid polymer. These plasticisers likewise preferably have lipophilic properties. The use of such plasticisers is known from the literature. Examples of these are:

ether, e.g. o-nitrophenyloctylether ester plasticisers, in this case particularly dicarboxylic acid diester plasticiser, tetracarboxylic acid, tetraester plasticiser, the esterising component being an aliphatic alcohol, generally with at least five carbon atoms, e.g. bis (2-ethyl hexyl) sebacate, diesters of phosphoric acid or phosphonic acid.

It is preferred according to the invention if a polymer and plasticiser and ion- or molecule-selective components are used, that the ion-selective or molecule-selective layers preferably consist of the following composition of the individual components:

20 to 40% by weight polymer material 50 to 75% by weight plasticiser 1 to 10% by weight ion-molecule-selective components It is particularly preferred if polymer membrane layers have the following composition:

30 to 35% by weight of polymer material 60 to 65% by weight plasticiser 1 to 5% by weight ion-molecule-selective components All membranes and membrane components which can be used according to prior art for manufacturing potentiometric electrodes, which are selective for neutral and charged species, can also be used for manufacturing the analyte-specific polymer membrane layer proposed according to the invention. In this respect an overview can be seen from the following source:

"CRC Handbook of ion-selective electrode: selectivity coefficients"/Ed.

Umezawa Y., CRC Press: Boca Raton, 1990; in Company periodicals e.g. Selectophpore (ionophore for ion-selective electrodes and optrodes) and Quasts, Crowns and Polyesters by Fluka Chemie AG.

Likewise, solid body material (e.g. crystalline bodies, monocrystals such as $LaF_3$ doped with $EU^{2+}$ for $F^-$, polycrystalline $Ag_2S$ blanks, ionic conductors (e.g. NASICON) or ion-selective glass (e.g. pH-pNa electrode glass) can be used.

A further variant of the invention now proposes to provide an analyte-specific polymembrane layer as described above additionally with an enzyme containing layer. In this way corresponding biosensors can now be produced. According to the invention, accordingly, there is formed on the analyte-specific polymembrane layer at least one further layer which contains an included or immobilised enzyme, and if necessary also a redox mediator. The method of operation of such a biosensor is based on the detection of the alteration in the electrical properties of the analyte-specific polymer membrane layer as a result of the biocatalytic activity of the enzyme in the additional enzyme-containing layer.

The material forming the layer preferably contains at least one macromolecular component which is preferably a protein, polysaccharide or synthetic polymer or copolymer.

There should be named among the preferred polymers the rnon-enzymatic proteins such as collagens and albumens. These proteins can be cross-linked in order to form a membrane for enzyme immobilisation.

As regards polysaccharides, the following examples are named:

Alginates; hitin; cellulose and its derivates such for example as nitrocellulose or esters and ethers of cellulose;

natural polymers such for example as polysaccharides have the advantage that inorganic catalysts are not present during polymerisation, which can be the case with synthetic polymers. Diethyl aminoethyl-dextrane (DEAE-Dextrane) or polyethylenimine can be used. Polysaccharides with a mole weight of 5,000 to 500,000, preferably from 5,000 to 50,000 should be selected.

Named among the suitable polymers are polyacrylamide gels; likewise vinyl polymers, particularly vinylacetates; polyvinyl alcohols, preferably polyvinyl butyral.

Also suitable are polyurethanes and polysiloxanes (also heteropolysiloxanes) which contain functional groups, e.g. amino groups.

In the case of albumen, cross-linking is preferably carried out with bi- or multi-functional reagents, e.g. glutaraldehyde and its oligomers. It should be mentioned that cross-linking is dependent on the exposure time with the glutaraldehyde, and this should lie between 10 and 90 minutes, preferably 30 minutes at ambient temperature.

The proportion of enzyme/(matrix component) is important for the diffusion properties of the membrane. The ratio here lies in the range of 5 to 100% by weight, preferably between 10 and 50% by weight.

The mechanical and adhesive properties of the enzymatic membranes can be improved if the solution forming the membrane contains a multivalent alcohol, preferably glycerol or sorbitol or lactitol. The preferred concentration of the multivalent alcohol lies in a range from 5 to 30% by volume.

The presence of a multivalent alcohol or polysaccharide in the solution from which the membrane is formed, can lead to better protection of the enzyme activity during immobilisation and thus to an extended life expectancy of the sensor.

With regard to immobilised redox enzymes, the enzymatic membrane can contain oxidising or reduced agents (e.g. ferrocene) which are capable of recycling the active centre of the enzyme.

Likewise, the enzyme can be immobilised on the analyte-selective layer by covalent bonding. This can be effected if the analyte-selective membrane carries appropriate functional groups (e.g. OH, —$NH_2$, or —COOH), or if an additional layer, containing appropriate functional groups, is formed on the analyte-selective membrane layer, so that the enzyme is bonded to the additional layer.

In order to reduce disturbances in interference, differential measurements can be carried out. In this case a differential signal between the ASIS can be measured with and without enzyme.

A further layer of cross-linked proteins or synthetic/natural polymer can be applied to the enzymatic layer. This layer improves the biosensor properties in the following way:

ensuring optimum conditions for the functional reliability of the enzyme;

reduction of the disadvantageous effect of the buffer capacity of the sample on the responsive behaviour of the biosensor;

enabling adjustment of the dynamic and linear range of the biosensor.

In order to suppress the negative influence of the buffer capacity for a buffer with weakly acidic groups and pK<7, the additional layer must carry functional groups which, at a given pH value of the sample, are negatively charged. For buffers with weakly basic residues and a pK>7, the functional groups must be positively charged during the assay conditions.

Further details, features and advantages of the present invention will become apparent from the following description of embodiments given by way of example and with reference to the drawings. Shown are:

FIG. 1: the schematic structure of a first embodiment of an analyte-selective sensor with an analyte-specific polymer membrane layer (chemosensor).

Figure 2:
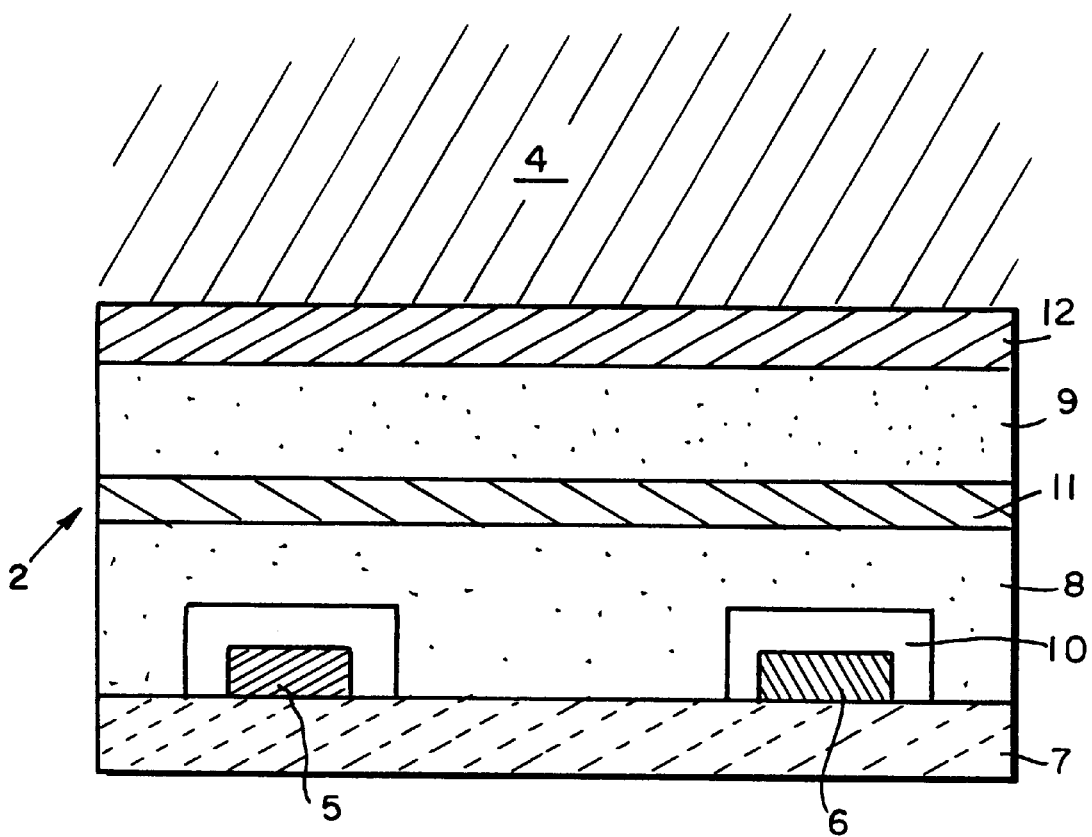

FIG. 2: shows the schematic structure of an analyte-selective sensor in the form of a biosensor.

FIG. 3a–d: show arrangements by way of example of measuring electrodes, in which the conductors are in the form of wires, or in the form of thick or thin layers.

FIG. 4a–d: show arrangements by way of example of measuring electrodes in which the conductors are in the form of disc electrodes.

FIG. 5a–d: show schematically the structure of the measuring electrodes in the form of IDEs and a measuring arrangement for measuring the admittance of the sensor.

Figure 6:
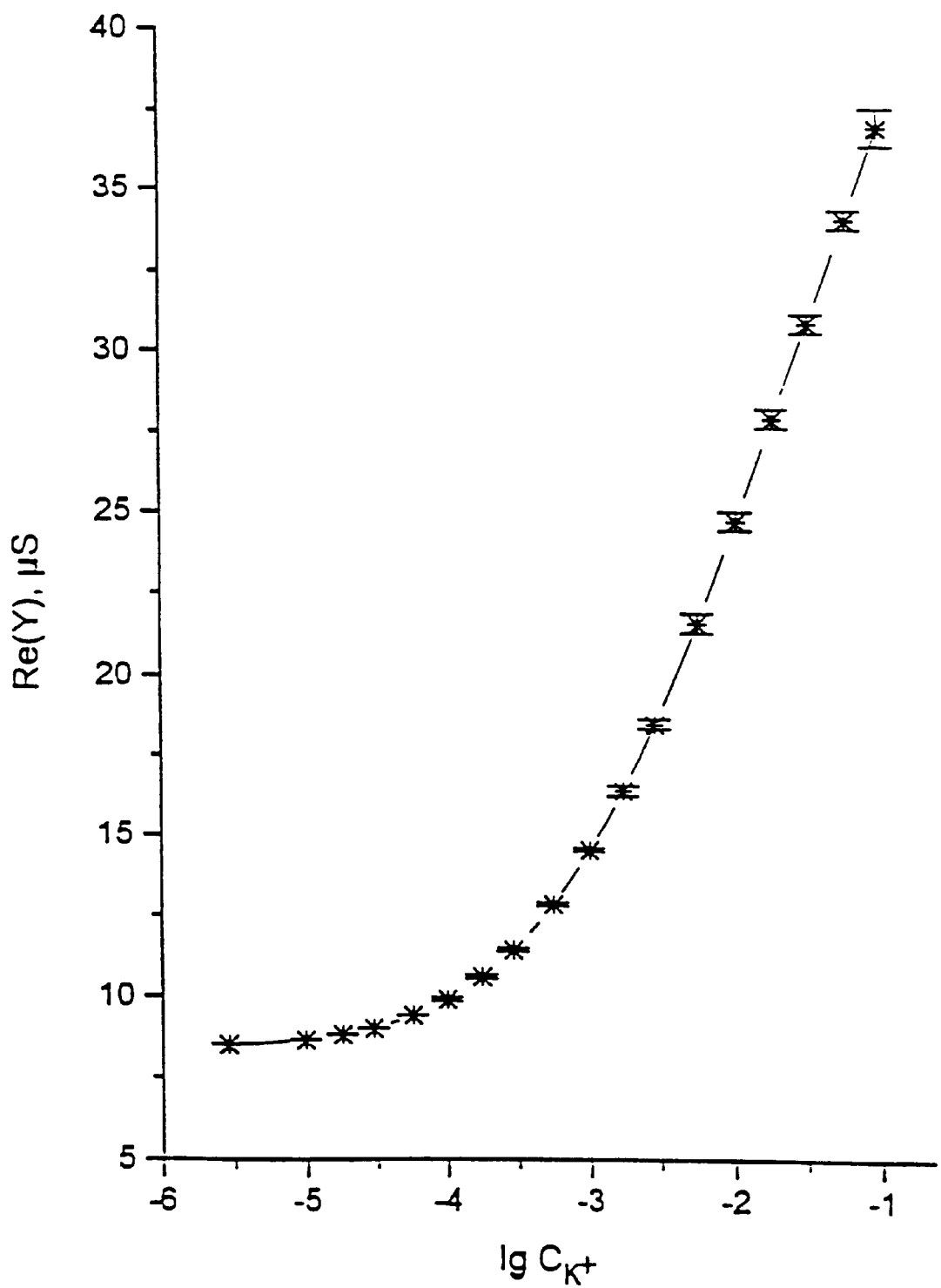

FIG. 6: shows the dependency of the real portion of the admittance, Re(Y), of the ASS on the basis of IDE, using PVC membranes containing valinomycin for detecting the concentration of $K^+$ in the solution. The measurements were carried out at 100 kHz. 1 M $NaNO_3$ was used as a background electrolyte.

Figure 7:
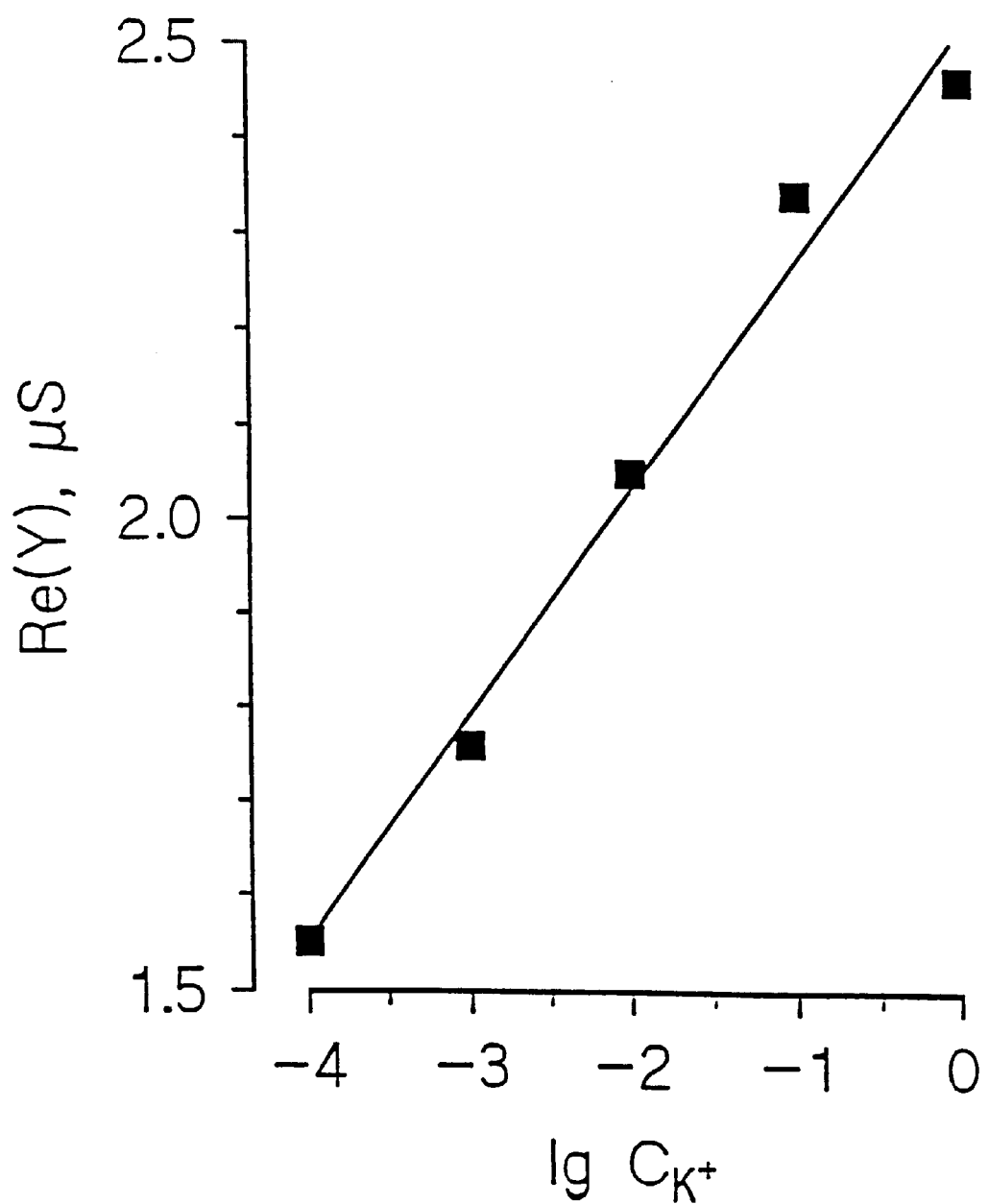

FIG. 7: shows the dependency of the real portion of the admittance, Re(Y), of the ASS based on two coated wire electrodes using membranes containing valinomycin to detect the concentration of $K^+$ in the solution. The measurements were carried out at 100 kHz, 1 M $NaNO_3$. was used as a background electrolyte.

Figure 8:
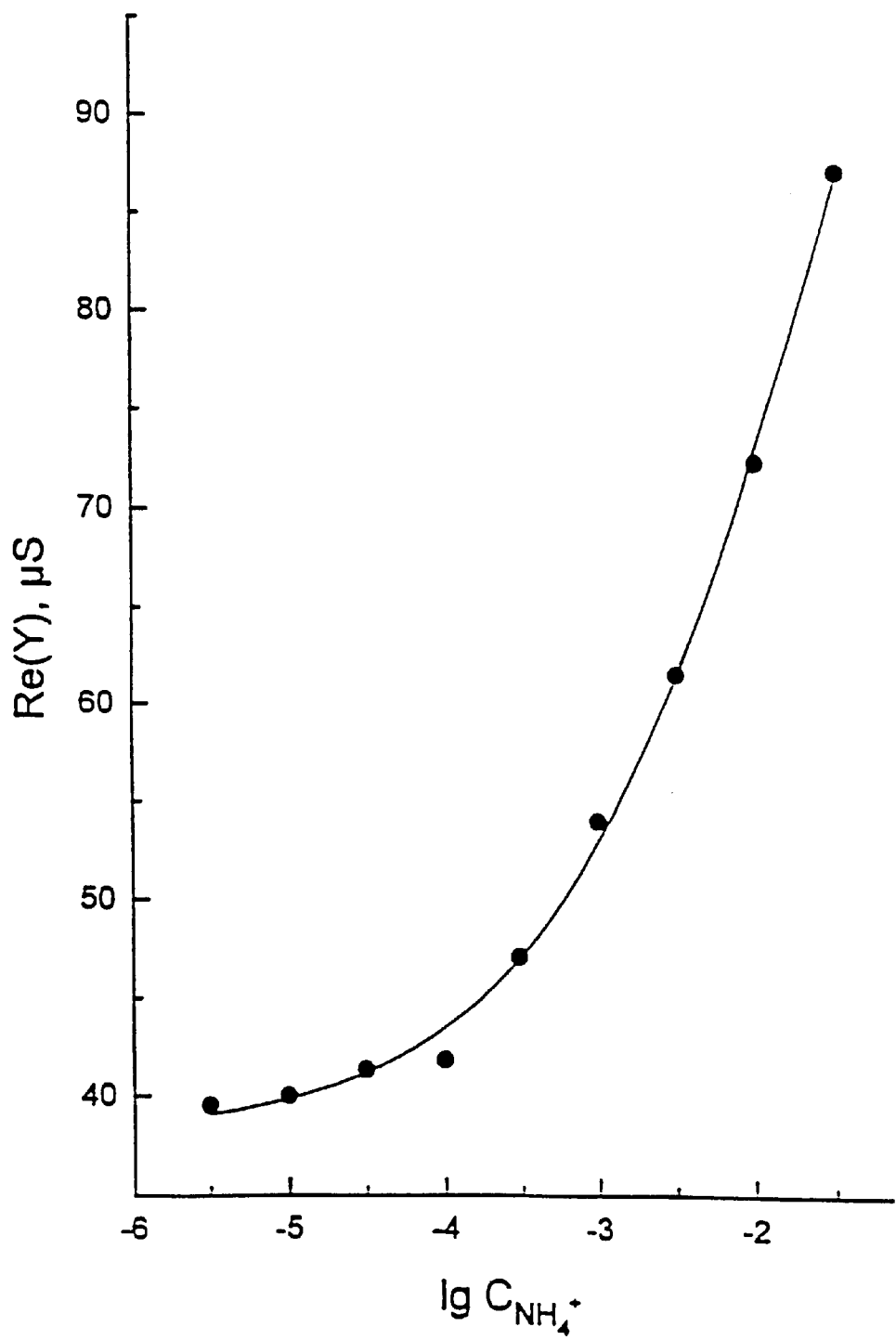

FIG. 8: shows the dependency of the real portion of the admittance, Re(Y) of the ASS on the basis of IDE, using PVC membranes containing nonactin to determine the concentration of $NH_4^-$ in the solution. The measurements were carried out at 100 kHz, 1 M $NaNO_3$ was used as a background electrolyte.

Figure 9:
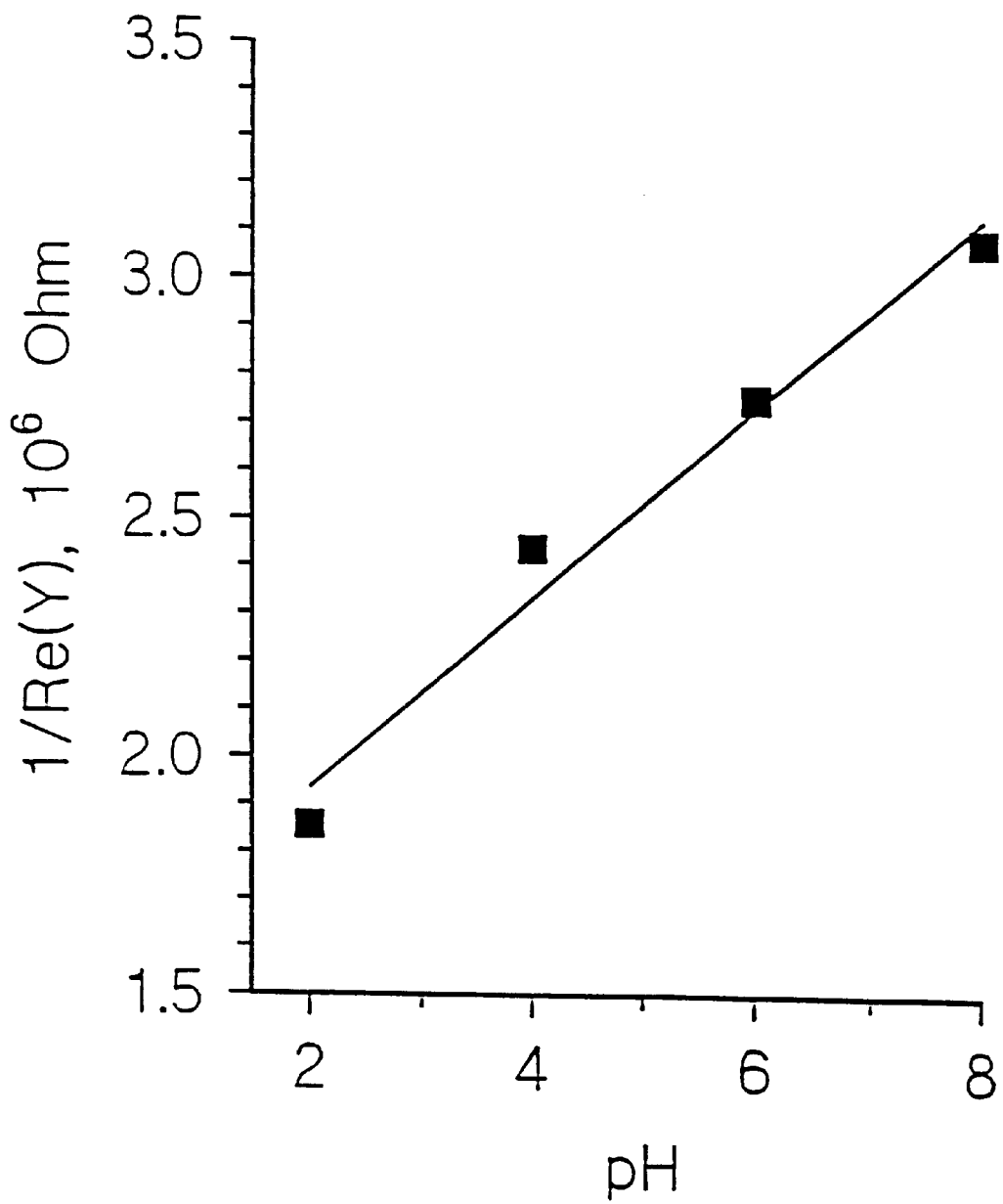

FIG. 9: shows the dependency of the reciprocal value of the real portion of the admittance, 1/Re(Y) of the ASS on the basis of IDE, using PVC membranes containing ETH-1907 ionophore to determine the pH value of the solution. Standard Merck buffers of differing pH values were used. The measurements were carried out at 100 kHz.

Figure 10:
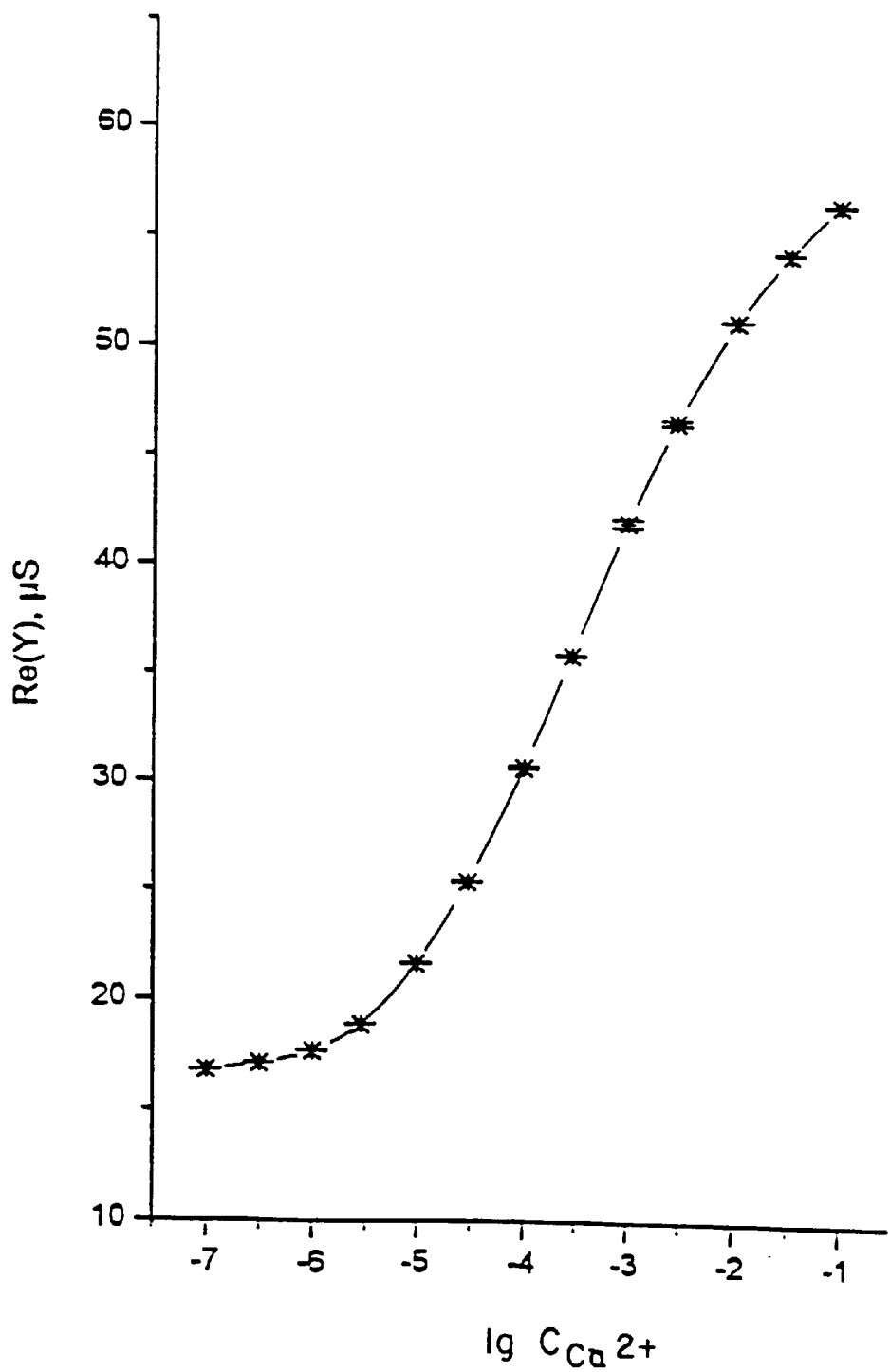

FIG. 10: shows the dependency of the real portion of the admittance, Re(Y) of the ASS on the basis of IDE, using PVC membranes containing Ca-IV ionophore by Fluka in order to determine the concentration of $Ca^{2+}$ in the solution. The measurements were carried out at 100 kHz, 1 M $NaNO_3$, was used as a background electrolyte.

FIG. 1 shows in cross-section the schematic structure of an analyte-selective sensor 1 according to the invention. The sensor 1 is in direct contact with the solution 4 and is so constructed that the analyte-specific polymer membrane layer 3 is applied to an inert carrier 7. The layer thickness of the sensitive layer 3 can lie in a range of 0.1 $\mu$m to 1 mm. In the embodiment according to FIG. 1 the electrodes 5, 6 have a direct contact with the layer 3. In the example in FIG. 1, this layer has the following composition:

32% by weight polymer material
66% by weight plasticiser and
2% by weight ion-selective components.

With such a composition of the analyte-specific polymer membrane layer the following sensors were produced:

1. Potassium-selective membrane: high-molecular polyvinylchloride homopolymerisate was used as a polymer material, the plasticer was o-nitrophenyloctyl ether. As a potassium-selective component a component known according to prior art was used, the natural antibiotic valinomycin.

2. Ammonium-selective membrane: high-molecular polyvinylchloride homopolymerisate was used as a polymer material, the plasticer was dibutyl sebacate. A component was used known from prior art as an ammonium-selective component, the natural antibiotic nonactin.

3. $H^-$-selective membrane: high-molecular polyvinyl chloride homopolymerisate was used as a polymer material, the phasticer was o-nitrophenyloctyl ether. A component known from prior art was used as an $H^{+-}$ selective component, ionophore ETH 1907 (4-nonadecyl pyridine).

4. $Ca^{2+}$-selective membrane: high-molecular polyvinyl chloride homopolymerisate was used as a polymer material, the plasticer was o-nitrophenyl octyl ether. A component known from prior art was used as a $Ca^{2+}$-selective component, Ca-IV ionophore of Fluka (N,N-dicyclohexyl-N', N'-dioctadecyl-3-oxpapentane diamide).

FIG. 2 now shows, similarly to the embodiment in FIG. 1, the schematic structure of a biosensor according to the invention. In the embodiment according to FIG. 2 the biosensor 2 consists of an analyte-specific polymer membrane 8 applied to a carrier 7. In the embodiment according to FIG. 2, the electrodes 5, 6 are now provided with an additional layer 10, which suppresses the boundary surface resistance. This layer 10 contains substances forming redox pairs according to CH 677 295. It is further provided in the embodiment in FIG. 2 that the polymer membrane layer 9 containing enzyme is not applied directly on to the analyte-specific polymer membrane 8, but that there is provided between these two layers a further layer 11, which serves for better bonding of the layer 9 to the layer 8. In this example this layer consists of carboxylised or aminised PVC and has a layer thickness of 10 $\mu$m to 1 mm. The enzyme-containing polymer membrane layer 9 can lie in a thickness range of 1 $\mu$m to 1 mm. The thickness of this layer preferably comes to 10 $\mu$m to 500 $\mu$m. In the example in FIG. 2 there is now also provided on the enzyme-containing polymer membrane layer 9 a further layer 12 of cross-linked protein or synthetic or natural polymer. This layer improves the biosensor properties in a favourable way. This layer in the example in FIG. 2 consists of Nafion or acetatecellulose and has a thickness of 100 $\mu$m.

According to the structure in FIG. 2, the following biosensors were manufactured:

1. Biosensors for urea and amino acid, the enzyme-containing polymer membrane layer 9 consisting of urease and amino acid oxidase respectively, and the analyte-specific polymer membrane layer 8 of ammonium-selective PVC membrane (ammonium ionophores).

2. Glucose or acetylcolin biosensors, here the enzyme-specific polymer membrane layer 9 then consisting of glucose-oxidase or acetylcolin esterase and the analyte-specific polymer membrane layer 8 is a pH-selective PVC membrane ($H^+$-ionophore).

FIG. 3 now shows by way of example arrangements of measuring electrodes such as can be used for the sensors according to the invention.

With respect to the practical execution of the measurements of the electrical properties of the layer, two basic types of measuring cells can be preferably distinguished, as shown in FIG. 3:

1. Both conductors (11) are covered by the layer (13) which in this way forms a continuous bulk phase (FIGS. 3 a, b);

2. Each of the conductors (11) is covered by the layer (13), but the layers do not form any continuous bulk phase (FIGS. 3, c, d);

3. Only one conductor is covered by the layer (13).

In the case 1 (see FIG. 3a) the proportion between the characteristic measurements of the layer (13) (thickness—d)

and those of the conductor (11) (smallest distance between the conductors—a, greatest width of the conductors along the connecting line—b), can be carried out with respect to two characteristic cases:

1.1 Either a or b or both are greater than d;

1.2 a and b are both smaller than d;

Cases 1.1, 2 and 3 are similar in the sense that in such arrangements the alteration in the conductivity of the solution tested, in which the sensor probe is immersed, contributes to the measured sensor output signal. Measurements of the specific-analyte concentration are however still possible if:

the background conductivity of the sample is constant;

the conductivity of the sample is very much greater than the conductivity of the analyte-specific membranes used.

the sensor characteristics in a standard solution of known or adjusted conductivity were determined before and after measurement in a solution.

parallel measurements of the conductivity of the sample were made and taken into consideration.

Case 1.2 corresponds to the situation when the proportion of volume conductivity of the sample at the sensor output signal is minimal, so that the measured signal principally corresponds to the bulk conductivity of the analyte-selective layer.

Figure 3A:
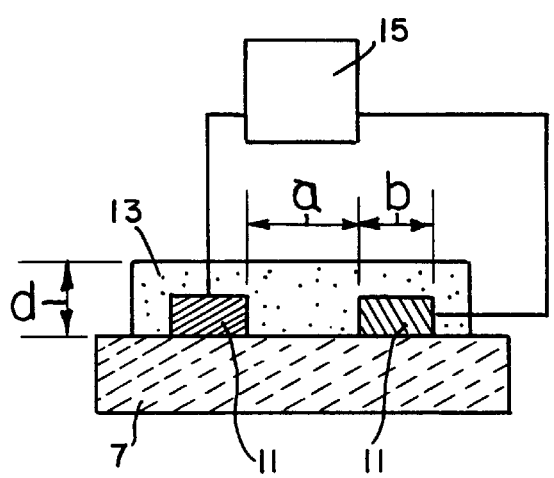
Figure 3B:
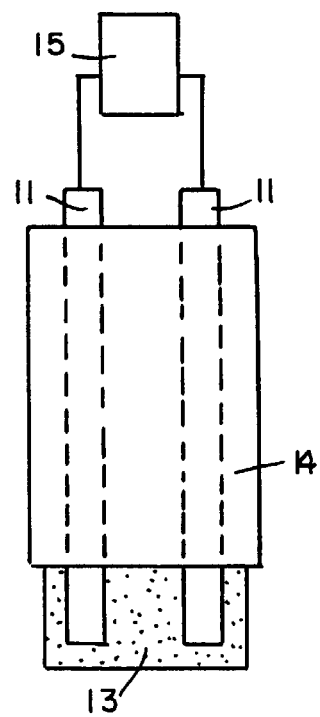
Figure 3C:
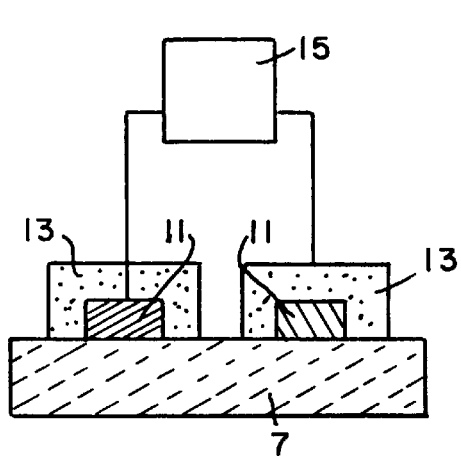
Figure 3D:
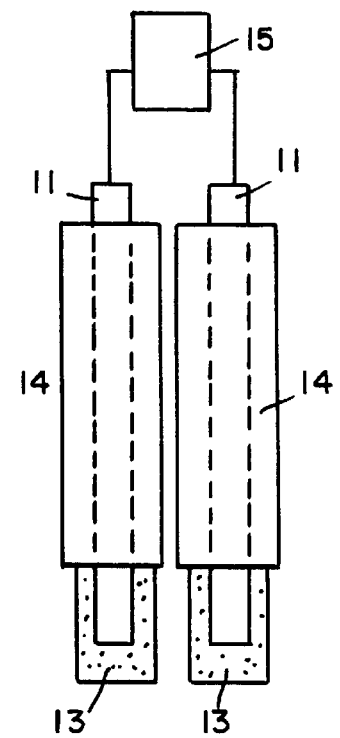
Figure 4A:
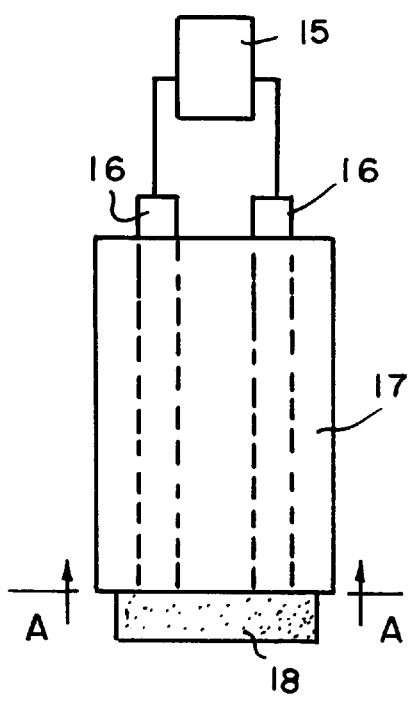
Figure 4B:
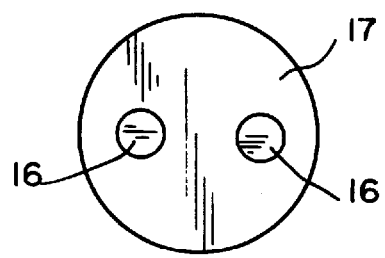
Figure 4C:
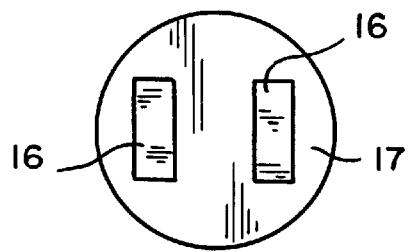
Figure 5A:
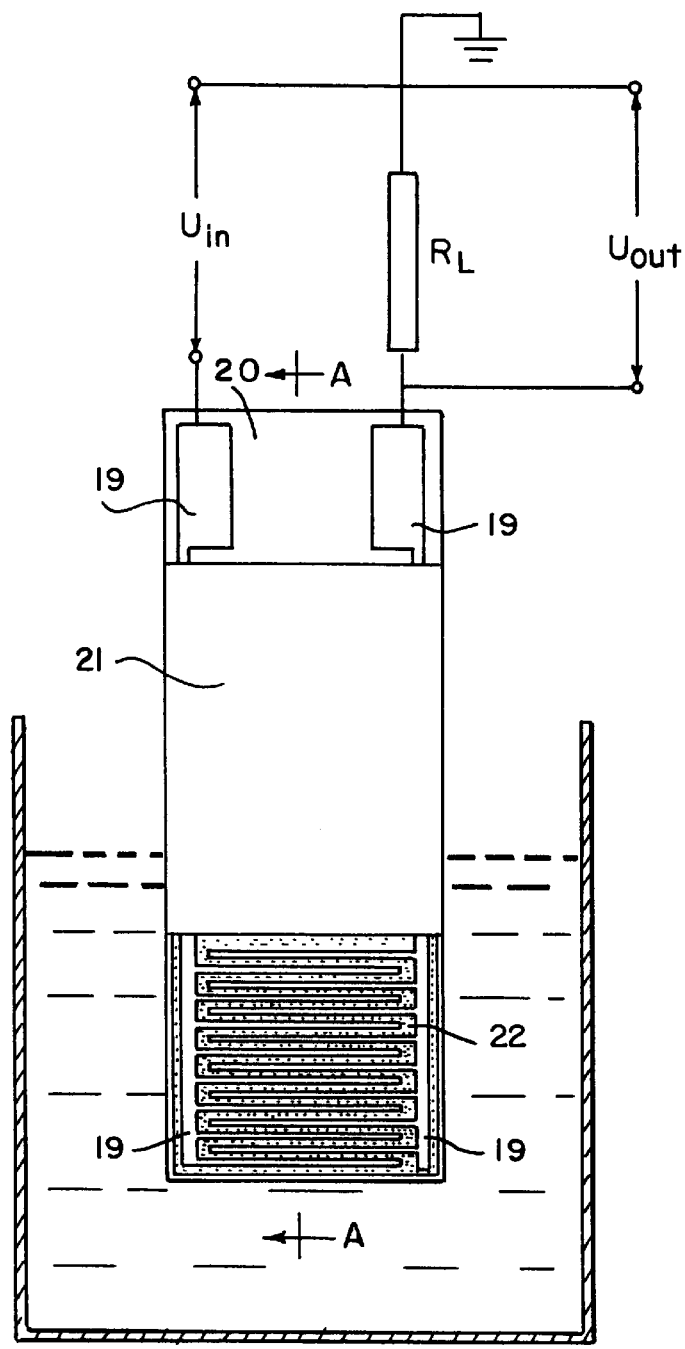
Figure 5B:
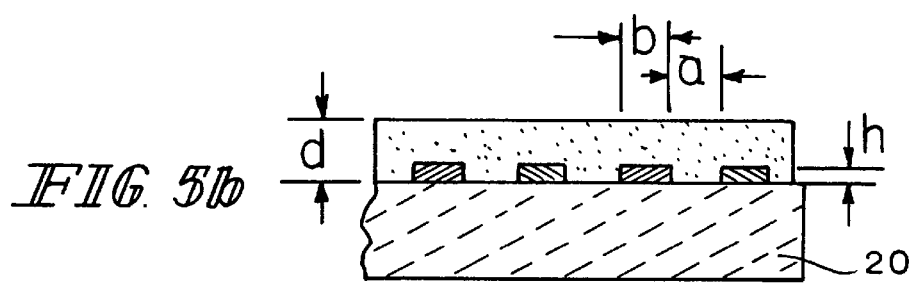

The invention basically embraces the following possible constructions of the sensor:

A wire electrodes (FIG. 3d). The sensor consists of two metal wires (11) which are covered as far as the ends at all points with an electrically insulating polymer (e.g. TFPE, PVC) or an inorganic (glass) layer (14) with a thickness of over 50 $\mu$m, better more than 100 $\mu$m, even better more than 500 $\mu$m. Instead of the metal wires, coaxial cables may also be used as measuring electrodes. One end of each wire (11) is connected to the measuring device (15). The analyte-selective layer (13) is applied to the other, exposed end of each wire (13). The thickness of the analyte-selective layer (13) thus formed should preferably be less than that of the insulating layer (14) covering the rest of the wire, particularly for the case where the layer has a very low conductivity. During measurements, the layer-covered areas of both wires are immersed in the test solution in such a way that they lie as close together as possible (FIG. 3c).

The advantage of such a construction resides in the extreme simplicity of manufacture.

B disc electrodes (FIG. 4). Two interconnected wires or strips (16) are pressed on or embedded in an electrically insulating plastic block (17) such as is shown in FIG. 4. The conductor ends projecting out of one side of the block are connected to the measuring device (15). The other side of the block (17) is polished, so that the collector electrodes form a flat surface in a plane with the surrounding surface of the plastic block. The analyte-selective layer is applied simultaneously to both electrodes or separately to each. Such a sensor probe can be directly immersed in the test solution or can be pressed by means of an o-ring on to a micro-flow meter cell.

One of the advantages of this construction resides in the simplicity of renewal of the probe simply by polishing the measuring surface of the electrodes.

C interdigital electrodes. Two interdigital electrodes (IDE) or conductor strips (19) are applied to an insulating substrate (20) (FIG. 5). The latter can in particular be a polymer strip (e.g. polyimide), glass, ceramics (e.g. molten aluminium or Sital) or sapphire. The electrode materials can be selected from those described above exactly like the analyte-specific layer (22). The areas of the electrodes connecting the measuring portion with the contact surfaces of the sensor chip must be covered by an electrically insulating layer (21) which leaves free only the electrical lead and the sensitive surface of the electrode (19). This passivation layer (21) can either be a polymer film (e.g. silicon rubber, high-temperature-cross-linked polyimide or photoresist) or inorganic films such as pyrolytic silicon oxide, CVD-silicon nitride or applied glass films.

The advantage in use of an IDE resides in the possibility of the dense arrangement of the electrodes (the dimensions a and d can be reduced down to the sub-micro scale) with a simultaneously large periphery, leading to an increase in the sensitivity of measurement over a small area. The lowest achievable threshold for the dimensions a and b lies at 0.1 $\mu$m, 2 $\mu$m or 50 $\mu$m, if electron photolithography, optical photolithography or screen printing technology are used to manufacture the electrodes. The thickness of the electrodes h usually lies between 0.01 $\mu$m and 10 $\mu$m.

The analyte-selective layer (22) is applied to the measuring surface of the IDE, which is free of passivation. The layer must cover the entire sensitive surface of the electrodes (19). As the electrical conductivity of the layer can be rather low (the resistance of a lipophilic ion-selective membrane on the basis of PVC can for example reach a level of $10^8$ $\Omega cm^2$), even small portions of the electrode directly exposed to the solution render reliable measurement of the membrane conductivity impossible, because its resistance is lower than the membrane resistance itself, and thus it can short-circuit the current flow in the measuring circuit.

In the case where the sensitive layer absorbs water, and has the same conductivity as the solution, the quality requirements of the passivation layer are of less importance, so that in some cases passivation is not necessary. This is for example the case when the surface of the measuring electrodes with the covering layer is much greater than the area of other portions of the electrode which are exposed to the solution.

The dimensions of a, b and h should as far as possible be selected so that the ratio 1.2 (s.o.) is fulfilled, i.e. the layer thickness d should at best be greater than a and b and h. The thickness of the passivation layer covering the central portion of the chip should preferably be greater than that of the measuring layer. In this case alterations in the background conductivity of the sample disturb measurement of the conductivity of the selective layer to the minimum degree.

The invention however included not only individual analyte probes, but also multi-analyte probes, which are produced by the combination or integration of multiple electrodes on a sensor unit or on a carrier, covered with layers specific for various analytes. Sensors of medium selectivity can likewise be integrated in a multi-sensor unit, leading to so-called "fingerprints" being obtained, which correspond to the various compositions of the sample solutions. Later, using various methods of pattern recognition, a corresponding sample composition can be associated to the respective response patterns. Thus the preferred construction of the multi-sensor is based on the use of microelectronic chips with the necessary number of pairs of integral digital electrodes described above, each pair being covered by the appropriate layer. Such a method of construction has the advantage of technical compatibility with IC technologies and of simplicity of miniaturisation.

Measurements of conductivity were carried out with the sensors produced according to the embodiment in FIG. 1 and FIG. 2.

A plurality of techniques are available for measuring the admittance or impedance of the sensor and thus for example the conductivity of the material-selective layer; said techniques can basically be divided into DC and AC techniques. (Cooper, W. D., Helfrick, A. D. E., Elektrische MeBtechnik [Electrical Measuring Technology], VCH: Weinheim, Base, Cambridge, N.Y., 1989). AC techniques are generally preferred, as they permit reduction of the signal to noise ratio and, particularly in our case of ion conductivity, prevent polarisation of concentration in the vicinity of the surfaces of the electrodes.

Alternatively, measurements can be carried out of bulk conductivity of layers by means of biopolar pulse techniques, described in Johnson, D. E. and Enke C. G., Biopolar pulse technique for fast conductance measurements, Analytical chemistry, 1970, vol. 42, pp. 329–335. The advantages of this technique consist in that they can be carried out rapidly (up to 10 $\mu s$) and are independent of parallel and serial scattering capacitances.

One of the simplest of the electrical arrangements for measuring the admittance (impedance) of the sensor and thus of the conductivity of the layer is shown in FIG. 5.

The load resistor $R_L$ is incorporated in series with the sensor to be investigated and the voltage drop at $R_L$ provides the output signal. When an AC input voltage is applied, the condition for use of such an arrangement is that, within the frequency range used of the input voltage, the impedance of the sensor tested, $Z_{sensor}$, should be considerably greater than $R_L$. In this case the current flow in the direction of the load resistor is mainly determined by the impedance of the sensor and can be easily calculated according to the formula $$I(\omega) = U_{out}(\omega)/R_L \quad (1)$$

Here w is the angular frequency of the input voltage $U_{in}$, and $U_{out}$ is the output voltage.

When an AC input voltage is applied, both the amplitude and the phase of the output signal (voltage or current) are frequency-dependent. The dispersion (frequency-dependency) of the output signal is principally determined under the conditions set above by the AC impedance of the tested sensor. The admittance of the sensor can be calculated with the formula $$Y = \frac{\text{Re}(U_{out})}{R_L|U_{inp}|} + i\frac{\text{Im}(U_{out})}{R_L|U_{inp}|} \quad (2)$$

The first term on the right-hand side represents the real portion of the sensor admittance $$\text{Re}(Y) = \frac{\text{Re}(U_{out})}{R_L|U_{inp}|} \quad (3)$$

which is proportional to the measured output signal and can be calculated with the aid of equation 3, on condition that $R_L$ and the amplitude of the input voltage are known.

In some measuring apparatus, instead of the admittance Y, the impedance Z of the sensor is measured. The impedance Z of a system represents the reciprocal value of the associated admittance. Impedance measurements therefore can likewise be used to categorise the conductivity of a layer.

In order to be able to follow the alterations in layer conductivity, in the preferred realisation of the invention the measurements of the admittance or alternatively of a phase component of the output signal of the order of measurement from FIG. 5 are used. These values are likewise dependent on the frequency, and this dependency can vary in the various frequency ranges. The normal operational frequency is selected, incorporating these factors, with the purpose of optimising the sensor sensitivity, reducing the requirements on the measuring device and suppressing non-specific interferences.

The preferred operational range in contact measurements lies at frequencies between 1 Hz and 100 kHz.

The preferred frequencies for contactless measurements of membrane conductivity are:

from 1 MHz to 100 MHz, when capacitive coupling is used;

from 10 Hz to 10,000 Hz, when inductive coupling is used.

EMBODIMENTS

1. Of the ASS on the basis of IDE

Two identical pairs of interdigital metal electrodes (Ni, PT or Au) were produced by vacuum evaporation on a ceramic substrate 0.5 mm thick. The dimensions of a sensor chip lie at 5 mm to 20 mm. For better adhesion, in the case of Pt or Au electrodes, an intermediate layer of chromium (0.1 $\mu m$ thick) was applied. Each electrode finger was 70 $\mu m$ wide and approximately 1 mm long with a spacing of 70 $\mu m$ between the electrode fingers of a pair. The sensitive surface of each electrode pair forming the impediometric transducer was approximately 1 mm to 1.5 mm. In order to define the sensitive surface of the sensor, the central portion of the chip was encapsulated with a layer of Dow Corning silicon rubber. The entire chip layout is shown schematically in FIG. 5.

2. Of ASS based on two coated wire electrodes (CWE)

Two silver wires with a diameter of 1 mm and a length of 3 cm were used. The central portion of each wire was encapsulated with a layer of Dow Corning silicon rubber, a piece 5 mm in length being left free on both sides of the wires.

The application of the ion-selective membrane on the sensitive surface of the IDE and CWE was effected by means of dip-coating from the solution of the membrane components in THF.

Measurements of the sensor admittance were carried out using an ONO SOKKI dual channel analyser CRF 940 or a lock-in amplifier EG & G 5209 corresponding to the measuring arrangement in FIG. 5.

EXAMPLE 1

The IDEs were coated with PVC membranes containing valinomycin. The dependency of the real portion Re(Y) and of the imaginary portion Im(Y) of the admittance of the sensor on the potassium concentration was tested in a frequency range of 0.05 Hz to 100 kHz. It was observed that Re(Y) at frequencies of 100 Hz to 100 kHz, corresponding to the membrane conductivity, increases with growing potassium concentration. The detection limit was in the range $10^{-5}$ M, even at 1 M sodium nitrate solution as an interfering ion electrolyte. At a frequency of 100 Hz the dependency Re(Y) against $pK^+$ was so to speak linear for the $pK^+$ in the region of 1 to 4 (FIG. 6).

A surprising fact was that, contrary to the data reported in the literature, Im(Y), the corresponding capacitive component of the sensor impedance, revealed none, or only an accidental dependency on the potassium concentration. This was also the case with the other examples.

EXAMPLE 2

The ASS on the basis of CWE (coated wire electrodes) using PVC membranes containing valinomycin, revealed a quasi-linear dependency of the Re(Y) on the pK in the region of 0 to 4 at 1 M sodium nitrate solution as an interfering ion electrolyte, measured at a frequency of 100 kHz (FIG. 7).

EXAMPLE 3

The ASS on the basis of IDE (interdigital electrodes) using PVC membranes containing nonactin revealed a dependency of the Re (Y) on the $pNH_4^+$ at 1 M sodium nitrate solution as an interfering ion electrolyte, measured at a frequency of 100 kHz (FIG. 8).

EXAMPLE 4

The ASS on the basis of IDE (interdigital electrodes) using pH-sensitive PVC membranes (ionophore ETH 1907) revealed quasi-linear dependency of the Re(Y) on the pH in a range of 2 to 8, measured at as frequency of 100 kHz (FIG. 9). Standard Merck buffers of various pH values were used.

EXAMPLE 5

The ASS on the basis of IDE (interdigital electrodes) using PVC membranes containing Ca-IV ionophore by Fluka revealed a dependency of the Re(Y) on the $Ca^{2+}$ concentration in the region of $10^{-7}$ to 0.1 M at 1 M sodium nitrate solution as an interfering ionelectrolyte, measured at a frequency of 100 kHz (FIG. 10).

We claim:

1. Analyte-selective sensor for at least one of qualitative and quantitative detection of at least one of ions and materials contained in solutions, wherein said sensor (1, 2) comprises at least one analyte specific layer (3, 8) of at least one of a liquid, solid and semi-solid material, in contact with the solution, applied to an inert carrier (7) and being solely ionically conductive, and which is in connection with at least two electrodes (5, 6), the layer (3, 8) containing coupling members which selectively remove the analyte from the solution, so that, by absorption of the analyte, at least one of the ionic resistance, the ionic conductivity, the ionic admittance and the ionic impedance of the layer (3, 8) is altered.

2. Analyte-selective sensor according to claim 1 wherein the electrodes (5, 6) are in direct contact with the analyte-specific layer (3, 8), and are constructed as one of two- and four-electrode arrangements.

3. Analyte-selective sensor according to claim 2 wherein the electrode materials are selected from the group consisting silver, gold, platinum, palladium, nickel, tantalum, titanium, chromium, copper, vanadium, aluminium, conductive pastes containing particles of metal or graphite, epoxy resins containing particles of metal or graphite, carbon based materials, highly doped silicon, conductive polymers and conductive polymers which contain particles of metal or graphite.

4. Analyte-selective sensor according to claim 2 wherein the electrode materials are at least one of electrical conductors, semiconductors and defect point conductors.

5. Analyte-selective sensor according to claim 2 wherein the electrodes (5, 6) are at least one of wire electrodes, disc electrodes and interdigital electrodes (IDE).

6. Analyte-selective sensor according to claim 1 wherein the electrodes (5, 6) are at least one of wire electrodes disc electrodes and interdigital electrodes (IDE).

7. Analyte-selective sensor according to claim 6 wherein the electrode materials are at least one of electrical conductors, semiconductors and defect point conductors.

8. Analyte-selective sensor according to claim 6 wherein the electrode materials are selected from the group consisting of silver, gold, platinum, palladium, nickel, tantalum, titanium, chromium, copper, vanadium, aluminium, conductive pastes containing particles of metal or graphite, epoxy resins containing particles of metal or graphite, carbon based materials, highly doped silicon, conductive polymers and conductive polymers which contain particles of metal or graphite.

9. Analyte-selective sensor according to claim 1 wherein the electrode materials are at least one of electrical conductors, semiconductors and defect point conductors.

10. Analyte-selective sensor according to claim 9 wherein the electrode materials are selected from the group consisting of silver, gold, platinum, palladium, nickel, tantalum, titanium, chromium, copper, vanadium, aluminum conductive pastes containing particles of metal or graphite, epoxy resins containing particles of metal or graphite, conductive pastes containing carbon-based materials, epoxy resins containing carbon-based materials, highly-doped silicon conductive polymers, and conductive polymers which contain particles of metal or graphite.

11. Analyte-selective sensor according to claim 10 wherein the electrode surface is roughened.

12. Analyte-selective sensor according to claims 1, 2, 6, 9, 10 or 11 wherein the electrodes (5, 6) are located directly on the carrier (7).

13. Analyte-selective sensor according to claim 1 further comprising at least one further layer (11) which contains at least one substance which is capable of forming a redox pair, said at least one further layer (11) being applied between the electrodes (5, 6) and the analyte-specific layer (3, 8) so that the resistance of the phase boundary is not increased.

14. Analyte-specific sensor according to claim 1 wherein the inert carrier (7) is selected from the group consisting of glass, paper, epoxy resin, plastic, polymer, sapphire and ceramic.

15. Analyte-selective sensor according to claim 1 wherein the carrier (7) is the inner surface of at least one of a capillary of a tube and an enclosed vessel.

16. Analyte-selective sensor according to claim 1 wherein the analyte-specific layer (3, 8) is a liquid which is capable of extracting the analyte selectively out of the solution (4) into the layer (3, 8).

17. Analyte-selective sensor according to claim 11 wherein the liquid is selected from the group consisting of non-polar liquids, aromatic hydrocarbons and saturated aliphatic hydrocarbons.

18. Analytical sensor according to claim 1 wherein the analyte-specific layer (3, 8) is a liquid which contains at least one of molecule-selective coupling members and ion-selective coupling members, so that the analyte is selectively extracted out of the solution (4) into the layer (3, 8).

19. Analyte-selective sensor according to claim 1 wherein the analyte-specific layer (3, 8) is a polymer, so that the analyte is selectively extracted out of the solution (4) into the layer (3, 8).

20. Analyte-selective sensor according to claim 19 wherein the analyte-specific layer (3, 8) is selected from the group consisting of polyethylene oxide film and polymer which has cation complexing properties and properties of separating ion pairs.

21. Analyte-selective sensor according to claim 20 wherein the analyte-specific layer (3, 8) contains alkali salts as ionic additives.

22. Analyte-selective sensor according to claim 19 wherein the polymer is produced by at least one of chemical, photochemical and electrochemical polymerisation of a polymerisable monomer selected from heteroaromatic/ aromatic compounds in the presence of free analyte molecules, with the analyte molecule then being washed out of the polymer so that, during membrane formation, "prints" of the analyte form on a molecular scale, which then act as coupling members with increased affinity to the analytes.

23. Analyte-selective sensor according to claim 19, wherein the polymer is a complex-forming polymer whose base polymers are selected from the group consisting polystyrols, polyacrylates, polyacrylnitrites, polyvinyl alcohols, polyethylenimines, polysiloxanes, polysaccharides, modified cellulose, starch, lignin, and chitin, the polymer being formed in the presence of at least one of complexing groups and chelate groups so that analyte-specific coupling members result.

24. Analyte-selective sensor according to claim 23 wherein the at least one of complexing groups and chelate groups are selected from the group consisting of iminodiacetic acid, hydroxyquinoline, thiourea, guanidine, dithiocarbamate, hydroxamic acid, amidoxin, aminophosphoric acid, (cyclic) polyamino, mercapto, 1,3-dicarbonyl residues, cage compounds (e.g. cyclophane, crown ether, antibiotics, cyclodextrine), antigens, antibodies, natural polypeptides, synthetic polypeptides, lectins, specific bonding proteins, lipids and tensides.

25. Analyte-selective sensor according to claim 19 wherein the polymer comprises polyions which have functional groups (coupling members) which can selectively bond at least one of anions and cations, so that during the selective bonding an alteration in the morphology of the polymer occurs.

26. Analyte-selective sensor according to claim 25 wherein the polymer is selected from the group consisting of proteoglycane and glycoproteins.

27. Analyte-selective sensor according to claim 19 wherein the analyte-specific layer (3, 8) comprises a crystalline liquid phase.

28. Analytc-selective sensor according, to claim 19 wherein the analyte-specific layer (3, 8) is formed from polylonic complexes between quaternary ammonium ions and further polyions.

29. Analyte-selective sensor according to claim 19 wherein the polymer is selected from the group consisting of ion exchangers and ionic polymers.

30. Analyte-selective sensor according to claim 29 wherein the polymer is selected from the group consisting of copolymers of ethylene, acrylic acid, metacrylic acid carboxy elastomers, terpolymers, terpolymer ethylene-propylene-diene sulphonate, substituted polyvinyls, perfluropolymers, and polyampholytes.

31. Analyte-selective sensor according to claim 19 wherein the polymer further contains at least one of ion-selective coupling members and molecule-selective coupling members.

32. Analyte-selective sensor according to claim 31 wherein the coupling members are selected from the group consisting of cation exchangers, anion exchangers, complex formers for cations, complex formers for anions and complex formers for neutral particles.

33. Analyte-selective sensor according to claim 31 or 32 wherein the complex formers are selected from the group consisting of crown ether, natural antibiotics, dicarboxylic acid diamides, tridodecylamine, guanidinium compounds, derivates of boric acid, calixarenes, cyclophanes, lipids, and tensides.

34. Analytc-selective sensor according to claim 19 wherein the polymer additionally contains a plasticiser.

35. Analyte-selective sensor according to claim 34 wherein the plasticiser is selected from the group consisting of ethers, ester plasticisers, diesters of phosphoric acid and diesters of phosphonic acid.

36. Analyte-selective sensor according to claim 1 wherein the analyte-specific layer (3, 8) is a polymer, which contains at least one of molecule-selective coupling members and ion-selective coupling members, so that the analyte is selectively extracted out of the solution (4) into the layer (3, 8).

37. Analyte-selective sensor according to claim 19 or 36 wherein the polymer comprises at least one of a homopolymerisate with an aliphatic main chain with low-polar or non-polar substituents and a copolymerisate with an aliphatic main chain with low-polar or non-polar substituents.

38. Analyte-selective sensor according to claim 37 wherein the substituents are selected from the group consisting of hydrogen, halogen, $NO_2$, COR, COOR, carboxylic acid nitrite groups, carboxylic acid amide groups, aliphatic/aromatic ether groupings and aromatic/heteroaromatic residues.

39. Analyte-selective sensor according to claim 19 or 36 wherein the polymer is selected from the group consisting of homopolymerisates, copolymerisates and monomer units, which originate from a halogenated alkene.

40. Analyte-selective sensor according to claim 39 wherein the substituents are selected from the group consisting of hydrogen, halogen, $NO_2$, COR, COOR, carboxylic acid nitrile groups, carboxylic acid amide groups, aliphatic ether groupings, aromatic ether groupings, aromatic residues and heteroaromatic residues.

41. Analyte-selective sensor according to claim 19 or 36 wherein the polymer is selected from the group consisting of substituted polyolefins, polysilanes, polysiloxanes, polyphosphazenes, polyesters, polyamides, polyurethanes and cellulose derivates.

42. Analyte-selective sensor according to claim 1 wherein the analyte-specific layer (3, 8) has a thickness of $1\mu$ to 1 mm.

43. Analyte-selective sensor according to claim 1 wherein the analyte-specific layer (3, 8) consists of 20 to 80% by weight polymer, 20 to 80% by weight plasticiser and 1 to 60% by weight of at least one of ion-selective components and molecule-selective components.

44. Analyte-selective sensor according to claim 1 wherein, in order to stabilise the analyte-specific layer (3, 8), a porous carrier/matrix (e.g. filter papers, textiles, glass) is used.

45. Analyte-selective sensor according to claim 1 wherein at least one further enzyme-containing layer (9) is applied to the analyte-specific layer (3, 8).

46. Analyte-selective sensor according to claim 45 wherein the layer (9) is selected from the group consisting of cross-linked proteins, natural polymers and their derivates, and synthetic polymers.

47. Analyte-selective sensor according to claim 46 wherein the enzymes are immobilized in the layer.

48. Analyte-selective sensor according to claim 45 wherein the proportion of enzyme to matrix component lies in the region of 5 to 100% by weight.

49. Analyte-selective sensor according to claim 1 further comprising an additional layer (11) between the analyte-specific layer (3, 8) and the enzyme-containing layer (9), said additional layer (11) selected from the group consisting of derivates of cellulose and vinyl polymers, and having functional groups, so that an improved bond formation is achieved.

50. Analyte-selective sensor according to claim 1 further comprising an additional layer (12) on at least one of the analyte-specific layer (3, 8) and the enzymatic layer (9), said additional layer being selected from the group consisting of copolymers of ethylene, acrylic acid, metacrylic acid, carboxy elastomers, terpolymers, terpolymer ethylene-propylene-diene sulphonate, substituted polyvinyls, perfluoropolymers and polyampholytes.

51. Analyte-selective sensor according to claim 1 wherein the electrode materials are selected from the group consisting of silver, gold, platinum, palladium, nickel, tantalum, titanium, chromium, copper, vanadium, aluminium, conductive pastes containing particles of metal or graphite, epoxy resins containing particles of metal or graphite, carbon based materials, highly doped silicon, conductive polymers and conductive polymers which contain particles of metal or graphite.

* * * * *